US011058372B2

(12) United States Patent
de Groot et al.

(10) Patent No.: US 11,058,372 B2
(45) Date of Patent: Jul. 13, 2021

(54) MAMMOGRAPHY APPARATUS AND METHOD OF PRESSURIZING A BREAST

(71) Applicant: Sigmascreening B.V., Enschede (NL)

(72) Inventors: Jeroen Emanuel de Groot, Enschede (NL); Cornelis Antonius Grimbergen, Enschede (NL); Gerard Johan den Heeten, Enschede (NL)

(73) Assignee: SIGMASCREENING B.V., Enschede (NL)

( * ) Notice: Subject to any disclaimer, the term of this patent is extended or adjusted under 35 U.S.C. 154(b) by 1 day.

(21) Appl. No.: 16/818,870

(22) Filed: Mar. 13, 2020

(65) Prior Publication Data

US 2020/0214652 A1 Jul. 9, 2020

Related U.S. Application Data

(63) Continuation of application No. PCT/NL2018/050717, filed on Oct. 29, 2018.

(30) Foreign Application Priority Data

Oct. 31, 2017 (NL) ...................................... 2019834

(51) Int. Cl.
*A61B 6/04* (2006.01)
*A61B 6/00* (2006.01)

(52) U.S. Cl.
CPC .......... *A61B 6/0487* (2020.08); *A61B 6/0414* (2013.01); *A61B 6/502* (2013.01); *A61B 6/54* (2013.01)

(58) Field of Classification Search
CPC ....... A61B 6/0457; A61B 6/54; A61B 6/0414; A61B 6/502; A61B 6/0435; A61B 6/44; A61B 6/586
See application file for complete search history.

(56) References Cited

U.S. PATENT DOCUMENTS

| 3,609,355 A | 9/1971 | Schwarzer |
| 5,099,503 A | 3/1992 | Strommer |

(Continued)

FOREIGN PATENT DOCUMENTS

| DE | 2014151 | 12/1971 |
| DE | 102006048607 | 4/2008 |

(Continued)

OTHER PUBLICATIONS

Khamapirad, T. , et al., "Diagnostic Imaging of Breat Cancer with LOIS: clinical feasibility", International Society for Optical Engineering, SPIE-INT, vol. 5697, No. 1, 2005, 35-44.

(Continued)

*Primary Examiner* — Don K Wong
(74) *Attorney, Agent, or Firm* — Peacock Law P.C.; Justin Muehlmeyer

(57) ABSTRACT

Mammography apparatus comprising an x-ray source, a movable paddle and a detector, wherein the paddle and the detector are arranged to cooperate for pressurizing a breast so as to prepare for x-ray imaging of the breast, wherein the paddle connects to a paddle drive control system that drives the paddle towards the detector with a selected speed, wherein the paddle drive control system connects to a speed controller which provides the paddle drive control system a variating target setpoint that sets a rate at which the paddle drive control system drives the paddle towards the detector, wherein the apparatus comprises a contact area measurement device with which the contact area of the breast with the paddle and/or the detector is measurable, and that the speed controller is only operable for varying the target setpoint of the paddle drive control system when the contact area measurement device establishes that the said contact area surpasses a predefined first threshold value.

9 Claims, 4 Drawing Sheets

(56) References Cited

U.S. PATENT DOCUMENTS

| | | |
|---|---|---|
| 5,335,257 A | 8/1994 | Stunberg |
| 5,355,715 A | 10/1994 | Rausche et al. |
| 5,590,166 A | 12/1996 | Suni et al. |
| 5,999,836 A | 12/1999 | Nelson et al. |
| 6,049,583 A | 4/2000 | Galkin et al. |
| 6,694,173 B1 | 2/2004 | Bende et al. |
| 7,558,367 B1 | 7/2009 | Tinwala et al. |
| 7,656,993 B2 | 2/2010 | Hoering |
| 7,734,013 B2 | 6/2010 | Kashiwagi et al. |
| 9,050,009 B2 | 6/2015 | Den Heeten et al. |
| 9,743,997 B2 | 8/2017 | Grimbergen et al. |
| 9,826,950 B2 | 11/2017 | Den Heeten et al. |
| 2005/0004458 A1 | 1/2005 | Kanayama et al. |
| 2006/0245541 A1 | 11/2006 | Aubel |
| 2006/0262903 A1 | 11/2006 | Diebold |
| 2007/0121782 A1 | 5/2007 | Sendai |
| 2008/0043904 A1 | 2/2008 | Hoernig |
| 2008/0080668 A1 | 4/2008 | Kashigawi |
| 2008/0103387 A1 | 5/2008 | Gross |
| 2008/0240346 A1 | 10/2008 | Kashiwagi et al. |
| 2008/0249415 A1 | 10/2008 | Okamura et al. |
| 2009/0262887 A1 | 10/2009 | Iordache et al. |
| 2009/0304146 A1 | 12/2009 | Ramsauer |
| 2012/0020455 A1 | 1/2012 | Fischer |
| 2012/0020464 A1 | 1/2012 | Matsuura |
| 2013/0028373 A1 | 1/2013 | Den Heeten et al. |
| 2014/0328458 A1 | 11/2014 | Erhard et al. |
| 2014/0341338 A1 | 11/2014 | Grimbergen et al. |
| 2015/0265186 A1 | 9/2015 | Kuwabara |
| 2015/0297150 A1* | 10/2015 | Grimbergen ......... A61B 6/0414 378/37 |
| 2019/0231290 A1 | 8/2019 | Den Heeten et al. |

FOREIGN PATENT DOCUMENTS

| | | |
|---|---|---|
| EP | 1493380 | 1/2005 |
| EP | 2009465 | 12/2008 |
| WO | 97/27801 | 8/1997 |
| WO | 01/17424 | 3/2001 |
| WO | 2011/102713 | 8/2011 |
| WO | 2013/076622 | 5/2013 |
| WO | 2013/129920 | 9/2013 |
| WO | 2013/162357 | 10/2013 |
| WO | 2018/067005 | 4/2018 |
| WO | 2019/004821 | 1/2019 |
| WO | 2019/088826 | 5/2019 |

OTHER PUBLICATIONS

Manohar, Sriang, et al., "Initial Results of in vivo Non-Invasive Cancer Imaging in the Human Breast Using Near-Infrared Photoacoustics", Optical Express, vol. 15, No. 19, 2007, 12277-85.

Vaartjes, Susanne E. et al., "First Clinical Trials of the Twente Photoacoustic Mammoscope (PAM)", International Society for Optical Engineering, Proceedings SPIE, vol. 6629, 2007, 662917-1-662917-12.

* cited by examiner

MAMMOGRAPHY APPARATUS AND METHOD OF PRESSURIZING A BREAST

CROSS-REFERENCE TO RELATED APPLICATIONS

This application is a continuation of International Patent Application No. PCT/NL2018/050717, entitled "Mammography Apparatus and Method of Pressurizing a Breast", filed on Oct. 29, 2018, which claims priority to Netherlands Patent Application No. 2019834, entitled "Mammography Apparatus and Method of Pressurizing a Breast", filed on Oct. 31, 2017, and the specification and claims thereof are incorporated herein by reference.

BACKGROUND OF THE INVENTION

U.S. Pat. No. 5,590,166 discloses a mammography apparatus according to the preamble, wherein a measurement device is used to measure a movement speed of the paddle towards the detector cover in a procedure for preparing the breast for subsequent x-ray imaging. The measurement of the movement speed is used to control the movement of respective movable parts of the known mammography apparatus.

A known problem in mammography as acknowledged by U.S. Pat. No. 5,590,166, is that compression of the breast inflicts pain on the patient.

It is also known that the pain sensation differs from one patient to the other; for instance persons with smaller breasts respond differently than persons with larger breasts. In fact from theoretical considerations and observations in research it can be demonstrated as being probable that the pain sensation increases progressively with smaller breast sizes.

U.S. Pat. No. 5,099,503 discloses a method for operating a mammography apparatus and such a mammography apparatus comprising an x-ray source, a movable paddle and a detector, wherein the paddle and the detector are arranged to cooperate for pressurizing a breast so as to prepare for x-ray imaging of the breast, wherein the paddle connects to a paddle drive control system that drives the paddle towards the detector with a selected speed, wherein the paddle drive control system connects to a speed controller which provides the paddle drive control system a variating target setpoint that sets a rate at which the paddle drive control system drives the paddle towards the detector.

BRIEF SUMMARY OF THE INVENTION

Embodiments of the present invention relate to a mammography apparatus comprising an x-ray source, a movable paddle and a detector, wherein the paddle and the detector are arranged to cooperate for pressurizing a breast so as to prepare for x-ray imaging of the breast, wherein the paddle connects to a paddle drive control system that drives the paddle towards the detector with a selected speed.

The invention is also embodied in a method for pressurizing the breast so as to prepare the breast for x-ray imaging.

It is an object of the invention to reduce or limit the pain sensation experienced by different persons, and to make this pain sensation less dependent on the size of the breast.

This object is achieved according to the invention by an apparatus and a method having the features of one or more of the appended claims.

According to one embodiment of the present invention, a mammography apparatus comprises a contact area measurement device with which the contact area of the breast with the paddle and/or the detector is measurable, and the speed controller is only operable for varying the target setpoint of the paddle drive control system when the contact area measurement device establishes that the said contact area surpasses a predefined first threshold value. In this way the apparatus is only functional when the pressurization forces can be distributed over a large enough breast contact area, which accordingly can limit the pain sensation during pressurization.

When the breast contact area is large enough the speed controller provides the paddle drive control system a variating target setpoint that sets a rate at which the paddle drive control system drives the paddle towards the detector, in particular the detector cover. When the mammography apparatus is provided with this feature it is possible to provide that pressurization of the breast is executed to gradually increase a pressure or force applied on the breast from an initial value to an eventual target value for the pressure or force which will be applied to the breast during x-ray imaging.

Within the scope of this invention the term "pressure" relates to the ratio of the force applied to the breast, and the contact area between the breast and the paddle and/or at the detector cover.

The gradual increase of the pressure or force applied on the breast provides that even persons having small breasts experience a reduced pain sensation. Accordingly the mammography apparatus of the invention preferably provides that the speed controller establishes a target setpoint of the paddle drive control system so as to control the pressurization of the breast to gradually increase to an eventual target value for the pressure or force applied to the breast.

Preferably the target setpoint of the paddle drive control system is adjusted at a rate to cause that the pressure applied to the breast increases with an amount in the range 1-2 kPa per second. When the pressure is adjusted at this rate it is desirable that the pressure applied to the breast increases in approximately 5-10 seconds to the eventual target value for the pressure or force applied to the breast.

It is further preferred that the initial pressure or force applied to the breast is set at a predefined second threshold value, and that the speed controller is only operable for varying the target setpoint of the paddle drive control system when the pressure or force applied to the breast surpasses the predefined second threshold value. This makes the system appropriate for use by an operator, who can then otherwise maintain the existing operating procedures.

BRIEF DESCRIPTION OF THE SEVERAL VIEWS OF THE DRAWINGS

The accompanying drawings, which are incorporated into and form a part of the specification, illustrate one or more embodiments of the present invention and, together with the description, serve to explain the principles of the invention. The drawings are only for the purpose of illustrating one or more embodiments of the invention and are not to be construed as limiting the invention. In the drawings.

DETAILED DESCRIPTION OF THE INVENTION

Figure 1:
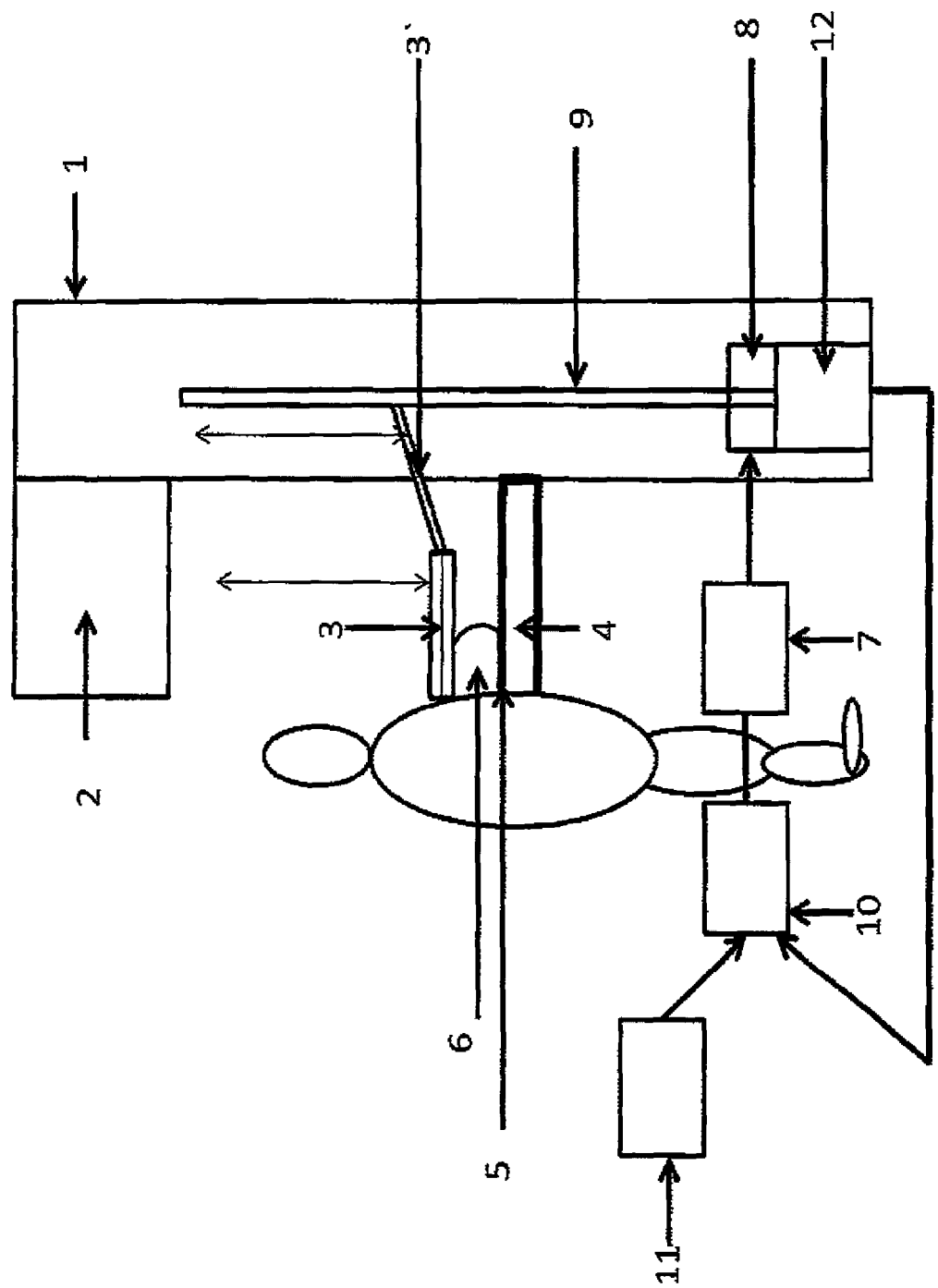
FIG. 1 shows schematically a mammography apparatus according to the invention.

Whenever in the figures the same reference numerals are applied, these numerals refer to the same parts.

Making reference first to FIG. 1 it shows a mammography apparatus 1 according to an embodiment of the present invention, which comprises an x-ray source 2, a movable paddle 3 and a detector 4 with a detector cover 5, wherein the paddle 3 and the detector 4 are arranged to cooperate for pressurizing a breast 6 so as to prepare for x-ray imaging of the breast 6.

Figure 3:
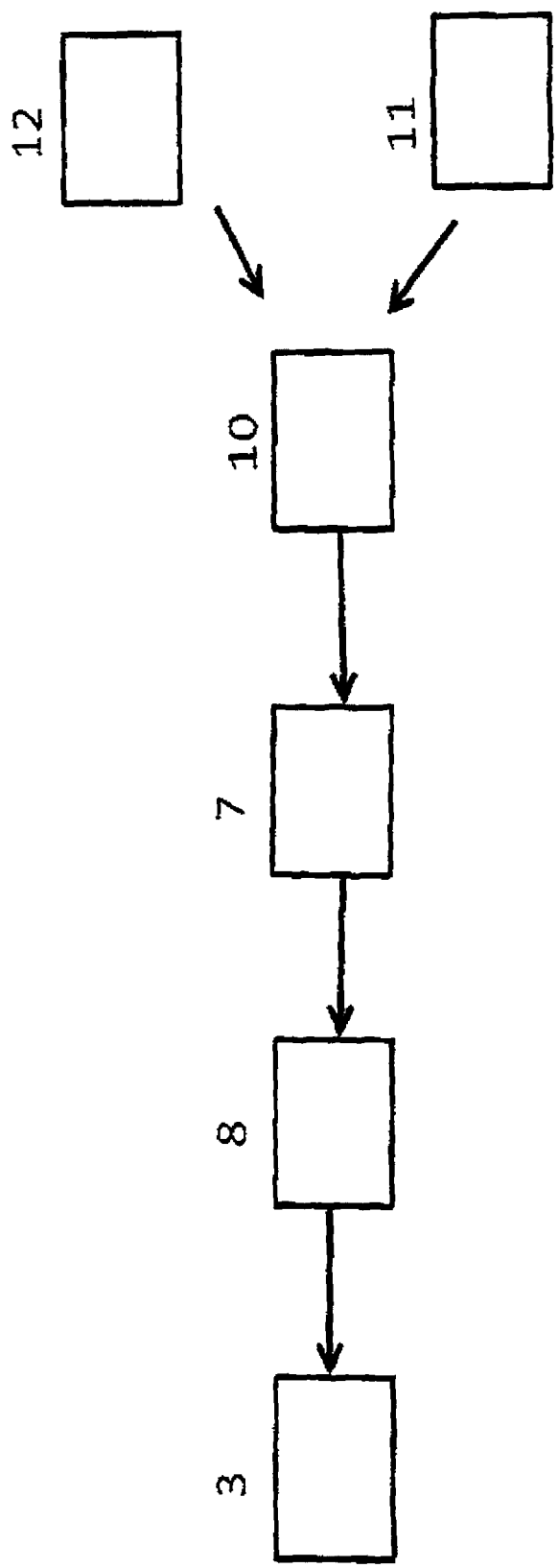
FIG. 3 shows schematically control circuitry of the mammography apparatus of the invention.

As more schematically shown in FIG. 3, the paddle 3 connects to a motor 8 that is controlled by a paddle drive control system 7 for moving the paddle 3. FIG. 1 shows that for this purpose the paddle 3 is connected via a paddle arm 3' to a spindle 9 that is driven by the motor 8. When the motor 8 rotates so does the spindle 9 which causes that the paddle 3 moves with a selected speed, which is determined by the rotational speed of the motor 8, towards the detector 4. It will be clear for the skilled person that instead of a motor driven spindle any other suitable drive system for the paddle 3 may be used, in particular since the drive system as such is not essential to the invention and is accordingly not mentioned in the independent claims.

FIGS. 1 and 3 show that the paddle drive control system 7 connects to a speed controller 10 which provides a variating target setpoint to the paddle drive control system 7. This variating target setpoint sets a rate at which the paddle drive control system 7 drives the paddle 3 towards the detector 4.

Figure 2:
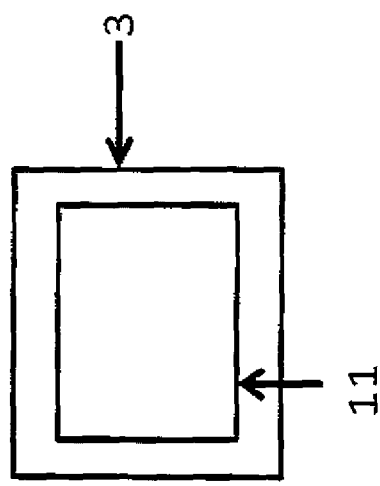
FIG. 2 shows a plan view at the paddle of the mammography apparatus of FIG. 1.

FIG. 1 further depicts that the mammography apparatus 1 comprises a sensor 12 which measures a force which corresponds to the force that the paddle 3 applies to the breast 6 which is being pressurized between the paddle 3 and the detector 4. Further the paddle 3 is provided with a contact area measurement sensor 11, for instance embodied as a radiolucent conductive film on the paddle 3 as shown in FIG. 2, which can be used to measure the contact area between the breast 6 and the paddle 3. The signals from the force sensor 12 and/or the contact area measurement sensor 11 are led to the speed controller 10, so as to enable that the speed controller 10 establishes a variating target setpoint setting the rate at which the breast 6 is pressurized so as to realize that the pressure on the breast 6 will be gradually increased, preferably at a constant rate in the range 1-2 kPa per second to an eventual target value for the pressure or force which will be applied to the breast 6 during x-ray imaging.

So as to arrange that the setpoint of the paddle drive control system 7 is based on an accurate measurement of the pressure that is applied to the breast 6, it is required to apply both the force sensor 12 and the contact area measurement sensor 11. It is of course possible to position the force sensor 12 and the contact area measurement sensor 11 at other locations than shown in the figures, or to base the sensors 11, 12 on other measurement principles then disclosed herein. The contact area measurement sensor 11 could for instance instead of being based on a conductive film on the paddle 3, alternatively be based on camera vision or other means of monitoring the contact area between the breast 6 and the paddle 3.

It is further preferred that the target setpoint of the paddle drive control system 7 is adjusted at a rate to cause that the pressure applied to the breast 6 increases with an amount in the range 1-2 kPa per second. The exact change rate of the pressure can then be selected and individualized with respect to the patient being subjected to the imaging by the mammography apparatus, for instance based on earlier experience with that patient. When the target setpoint of the drive control system 7 is adjusted at a rate in the range 1-2 kPa per second, it is preferable that the pressure applied to the breast 6 increases in approximately 5-10 seconds to the eventual target value for the pressure or force applied to the breast 6. This is all clearly shown in FIG. 4 in which the preparatory deformation period 1/5-5/5 corresponds to the 10 seconds that are used for pressurizing the breast 6. Thereafter the clamping period of the breast 6 starts in which the actual x-ray imaging of the breast takes place.

The apparatus 1 comprises a contact area measurement device 11 with which the contact area of the breast 6 with the paddle 3 and/or the detector 4 is measurable, and the speed controller 10 can be arranged to be only operable for varying the target setpoint of the paddle drive control system 7 when the contact area measurement device 11 establishes that the said contact area surpasses a predefined first threshold value. This restriction in the operation of the speed controller 10 is desirable when the actual pressure is used to determine the setpoint of the paddle drive control system 7.

It is further desirable that an initial pressure or force applied to the breast 6 is set at a predefined second threshold value, and that the speed controller 10 is only operable for varying the target setpoint of the paddle drive control system 7 when the pressure or force applied to the breast 6 surpasses the predefined second threshold value.

Figure 4:
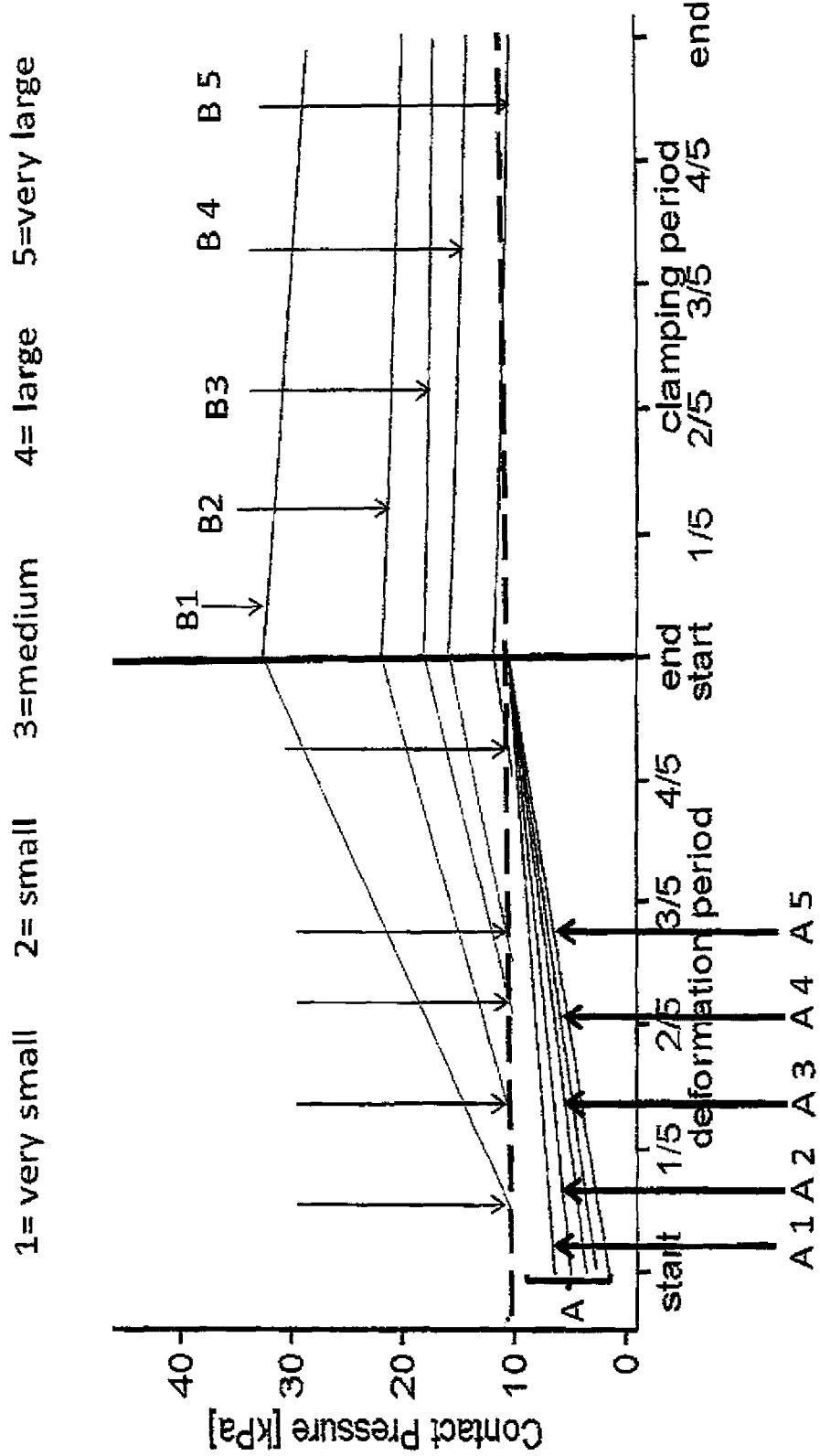
FIG. 4 shows a time pressure diagram showing in comparison the results from a mammography apparatus of the prior art and the mammography apparatus of the invention.

FIG. 4 represents with the graphs A pressurization of breasts of five different sizes based on quintiles of a normal population, graph A1 representing a small size breast, graphs A2, A3 and A4 representing midsize breasts, and graph A5 representing a relatively large breast. The graphs B1, B2, B3, B4 and B5 respectively show the results of pressurizing breasts of small size, midsizes and large size using a mammography apparatus in accordance with the prior art. From these graphs it is clear that particularly small size breasts are expected to suffer from pain sensations in the apparatus of the prior art, whereas the invention provides that the subjective pain sensations which may be expected to be experienced by persons with different breast sizes are brought at the same level when using the same rate of pressurizing.

Although the invention has been discussed in the foregoing with reference to an exemplary embodiment of the mammography apparatus of the invention, the invention is not restricted to this particular embodiment which can be varied in many ways without departing from the invention. The discussed exemplary embodiment shall therefore not be used to construe the appended claims strictly in accordance therewith. On the contrary the embodiment is merely intended to explain the wording of the appended claims without intent to limit the claims to this exemplary embodiment. The scope of protection of the invention shall therefore be construed in accordance with the appended claims only, wherein a possible ambiguity in the wording of the claims shall be resolved using this exemplary embodiment.

Embodiments of the present invention can include every combination of features that are disclosed herein independently from each other. Although the invention has been described in detail with particular reference to the disclosed embodiments, other embodiments can achieve the same results. Variations and modifications of the present invention will be obvious to those skilled in the art and it is intended to cover in the appended claims all such modifications and equivalents. The entire disclosures of all references, applications, patents, and publications cited above are hereby incorporated by reference. Unless specifically stated as being "essential" above, none of the various components or the interrelationship thereof are essential to the operation of the invention. Rather, desirable results can be achieved by substituting various components and/or reconfiguration of their relationships with one another.

Note that in the specification and claims, "about" or "approximately" means within twenty percent (20%) of the numerical amount cited. All computer software disclosed herein may be embodied on any non-transitory computer-readable medium (including combinations of mediums), including without limitation CD-ROMs, DVD-ROMs, hard drives (local or network storage device), USB keys, other removable drives, ROM, and firmware.

The invention claimed is:

1. Mammography apparatus comprising:
   an x-ray source;
   a movable paddle; and
   a detector;
   wherein the paddle and the detector are arranged to cooperate for pressurizing a breast so as to prepare for x-ray imaging of the breast;
   wherein the paddle connects to a paddle drive control system configured to drive the paddle towards the detector with a selected speed;
   wherein the paddle drive control system connects to a speed controller which provides the paddle drive control system a variating target setpoint that sets a rate at which the paddle drive control system drives the paddle towards the detector;
   wherein the apparatus further comprises a contact area measurement device with which the contact area of the breast with the paddle and/or the detector is measurable; and
   wherein the speed controller is only operable for varying the target setpoint of the paddle drive control system when the contact area measurement device establishes that the said contact area surpasses a predefined first threshold value.

2. Mammography apparatus according to claim 1, wherein the speed controller establishes a target setpoint of the paddle drive control system so as to control the pressurization of the breast to gradually increase to an eventual target value for the pressure or force applied to the breast.

3. Mammography apparatus according to claim 2, wherein the target setpoint of the paddle drive control system is adjusted at a rate to cause the pressure applied to the breast to increase with an amount in the range of about 1-2 kPa per second.

4. Mammography apparatus according to claim 2, wherein the target setpoint of the paddle drive control system is adjusted at a rate to cause the pressure applied to the breast to increase in approximately 5-10 seconds to the eventual target value for the pressure or force applied to the breast.

5. Mammography apparatus according to claim 1, wherein an initial pressure or force applied to the breast is set at a predefined second threshold value, and that the speed controller is only operable for varying the target setpoint of the paddle drive control system when the pressure or force applied to the breast surpasses the predefined second threshold value.

6. Method for x-ray imaging of a breast with a mammography apparatus comprising:
   pressurizing a breast using a movable paddle and a detector, so as to prepare for x-ray imaging of the breast using an x-ray source, wherein the pressurization of the breast is executed at a variating rate; and
   measuring the contact area of the breast with the paddle and/or with the detector, wherein the rate for the pressurization of the breast is only varied when it is established that the measured contact area of the breast with the paddle and/or with the detector surpasses a predefined first threshold value.

7. Method according to claim 6, wherein the pressurization of the breast is executed to gradually increase a pressure or force applied on the breast to an eventual target value for the pressure or force applied to the breast which will be present during x-ray imaging.

8. Method according to claim 6, wherein the pressure applied to the breast is provided to increase with an amount in the range of about 1-2 kPa per second.

9. Method according to claim 7, wherein the pressure applied to the breast is provided to increase in approximately 5-10 seconds to the eventual target value for the pressure or force applied to the breast.

* * * * *